US010646845B2

(12) United States Patent
Bhandarkar et al.

(10) Patent No.: US 10,646,845 B2
(45) Date of Patent: May 12, 2020

(54) COOLING BETWEEN MULTIPLE POLYOLEFIN POLYMERIZATION REACTORS

(71) Applicant: Chevron Phillips Chemical Company, LP, The Woodlands, TX (US)

(72) Inventors: Maruti Bhandarkar, Kingwood, TX (US); Elizabeth A Benham, Spring, TX (US); Rebecca A. Gonzales, Houston, TX (US); Joel A Mutchler, Kingwood, TX (US); Catherine M. Gill, Kingwood, TX (US); Timothy O. Odi, Kingwood, TX (US); Thanh T. Nguyen, Sugar Land, TX (US); Scott E. Kufeld, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 970 days.

(21) Appl. No.: 13/934,627

(22) Filed: Jul. 3, 2013

(65) Prior Publication Data
US 2015/0011814 A1    Jan. 8, 2015

(51) Int. Cl.
*B01J 19/18*    (2006.01)
*C08F 2/01*    (2006.01)
(Continued)

(52) U.S. Cl.
CPC ....... *B01J 19/0013* (2013.01); *B01J 19/1818* (2013.01); *B01J 19/1837* (2013.01);
(Continued)

(58) Field of Classification Search
None
See application file for complete search history.

(56) References Cited

U.S. PATENT DOCUMENTS 2,964,514 A * 12/1960 Fawcett .................. C08F 10/00
526/106
4,113,440 A * 9/1978 Klaasen .................. B01J 10/00
137/3
(Continued)

FOREIGN PATENT DOCUMENTS

EP    2030678    3/2009
EP    2336200 A1 †  6/2011
(Continued)

OTHER PUBLICATIONS

International Search Report for PCT/US2014/044593 dated Sep. 30, 2014.
(Continued)

*Primary Examiner* — Jennifer A Leung
(74) *Attorney, Agent, or Firm* — Eversheds Sutherland (US) LLP

(57) ABSTRACT

A system and method for a first reactor to produce a transfer slurry having a first polyolefin polymerized in the first reactor, a heat-removal zone to remove heat from the transfer slurry, and a second reactor to receive the transfer slurry cooled by the heat-removal zone, the second reactor to produce a product slurry having a product polyolefin which includes the first polyolefin and a second polyolefin polymerized in the second reactor.

15 Claims, 3 Drawing Sheets

(51) Int. Cl.
*B01J 19/00* (2006.01)
*C08F 110/02* (2006.01)
*C08J 11/02* (2006.01)
*C08F 2/00* (2006.01)
*C08F 6/00* (2006.01)
*C07C 2/06* (2006.01)
*C08F 10/00* (2006.01)

(52) U.S. Cl.
CPC ............... *C07C 2/06* (2013.01); *C08F 2/001* (2013.01); *C08F 6/001* (2013.01); *C08F 10/00* (2013.01); *C08F 110/02* (2013.01); *C08J 11/02* (2013.01); *B01J 2219/0004* (2013.01); *B01J 2219/00054* (2013.01); *B01J 2219/00094* (2013.01); *B01J 2219/00103* (2013.01); *B01J 2219/00123* (2013.01); *B01J 2219/00128* (2013.01); *B01J 2219/00247* (2013.01); *C08F 2/01* (2013.01)

(56) References Cited

U.S. PATENT DOCUMENTS

| | | | | |
|---|---|---|---|---|
| 4,229,416 | A | * | 10/1980 | Donaldson ................. B01J 8/26 422/134 |
| 4,306,041 | A | * | 12/1981 | Cozewith ............... C08F 210/18 526/119 |
| 4,424,341 | A | † | 1/1984 | Hanson |
| 4,496,698 | A | * | 1/1985 | Adriaans .................. B01J 19/18 526/352 |
| 5,235,852 | A | | 8/1993 | Toedtli |
| 6,063,878 | A | * | 5/2000 | Debras .................... C08F 10/02 526/106 |
| 6,235,852 | B1 | * | 5/2001 | Hess .................... B01J 19/0013 165/65 |
| 6,753,387 | B1 | | 6/2004 | Tait et al. |
| 7,033,545 | B2 | | 4/2006 | Kufeld et al. |
| 7,034,092 | B2 | | 4/2006 | Marechal |
| 2009/0228259 | A1 | | 9/2009 | Gupta et al. |

FOREIGN PATENT DOCUMENTS

| | | | |
|---|---|---|---|
| EP | 2336201 | A1 † | 6/2011 |
| EP | 2557093 | | 2/2013 |
| GB | 860376 | A * | 2/1961 .......... B01J 19/0013 |
| WO | 2008/141965 | | 11/2008 |
| WO | 2008/141965 | A1 † | 11/2008 |
| WO | 2009/030646 | A1 † | 3/2009 |
| WO | 2009/030647 | A1 † | 3/2009 |
| WO | 2009101008 | | 8/2009 |
| WO | WO 2011076371 | A1 * | 6/2011 .......... B01J 19/0013 |
| WO | 2013073595 | A1 | 5/2013 |

OTHER PUBLICATIONS

Catalysts for Olefin Coordination Polymerization and Polyolefins, edited by Shijing Xiao, Fusheng, Yu, Beijing University of Technology Press, Dec. 2002, 1st Edition, pp. 148-149, Translated.

Industrial Polymerization Reactor, edited by Kai Wang, Jianzhong Sun, China Petrochemical Press, Apr. 1997, 1st Edition, pp. 320-324, Translated.

\* cited by examiner
† cited by third party

COOLING BETWEEN MULTIPLE POLYOLEFIN POLYMERIZATION REACTORS

BACKGROUND

1. Field of the Invention

The present invention relates generally to polyolefin production with multiple polymerization reactors and, more particularly, to cooling a polyolefin transfer slurry between polymerization reactors.

2. Description of the Related Art

This section is intended to introduce the reader to aspects of art that may be related to aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

As chemical and petrochemical technologies have advanced, the products of these technologies have become increasingly prevalent in society. In particular, as techniques for bonding simple molecular building blocks into longer chains (or polymers) have advanced, the polymer products, typically in the form of various plastics, have been increasingly incorporated into everyday items. Polyolefin polymers such as polyethylene, polypropylene, and their copolymers, are used for piping, retail and pharmaceutical packaging, food and beverage packaging, plastic bags, toys, carpeting, various industrial products, automobile components, appliances and other household items, and so forth.

Specific types of polyolefins, such as high-density polyethylene (HDPE), have particular applications in the manufacture of blow-molded and injection-molded goods, such as food and beverage containers, film, and plastic pipe. Other types of polyolefins, such as low-density polyethylene (LDPE), linear low-density polyethylene (LLDPE), isotactic polypropylene (iPP), and syndiotactic polypropylene (sPP) are also suited for similar applications. The mechanical requirements of the application, such as tensile strength and density, and/or the chemical requirements, such thermal stability, molecular weight, and chemical reactivity, typically determine what type of polyolefin is suitable.

One benefit of polyolefin construction, as may be deduced from the list of uses above, is that it is generally non-reactive with goods or products with which it is in contact. This allows polyolefin products to be used in residential, commercial, and industrial contexts, including food and beverage storage and transportation, consumer electronics, agriculture, shipping, and vehicular construction. The wide variety of residential, commercial and industrial uses for polyolefins has translated into a substantial demand for raw polyolefin which can be extruded, injected, blown or otherwise formed into a final consumable product or component.

To satisfy this demand, various processes exist by which olefins may be polymerized to form polyolefins. These processes may be performed at or near petrochemical facilities, which provide ready access to the short-chain olefin molecules (monomers and comonomers), such as ethylene, propylene, butene, pentene, hexene, octene, decene, and other building blocks of the much longer polyolefin polymers. These monomers and comonomers may be polymerized in a liquid-phase polymerization reactor and/or gas-phase polymerization reactor. As polymer chains develop during polymerization in the reactor, solid particles known as "fluff" or "flake" or "powder" are produced in the reactor.

The fluff may possess one or more melt, physical, rheological, and/or mechanical properties of interest, such as density, melt index (MI), melt flow rate (MFR), comonomer content, molecular weight, crystallinity, and so on. Different properties for the fluff may be desirable depending on the application to which the polyolefin fluff or subsequently pelletized polyolefin is to be applied. Selection and control of the reaction conditions within the reactor, such as temperature, pressure, chemical concentrations, polymer production rate, catalyst type, and so forth, may affect the fluff properties.

In addition to the one or more olefin monomers, a catalyst (e.g., Ziegler-Natta, metallocene, chromium-based, post-metallocene, nickel, etc.) for facilitating the polymerization of the monomers may be added to the reactor. For example, the catalyst may be a particle added via a reactor feed stream and, once added, suspended in the fluid medium within the reactor. Unlike the monomers, catalysts are generally not consumed in the polymerization reaction. Moreover, an inert hydrocarbon, such as isobutane, propane, n-pentane, i-pentane, neopentane, n-hexane, and/or heptane, and so on, may be added to the reactor and utilized as a diluent to carry the contents of the reactor. However, some polymerization processes may employ monomer as the diluent, such as in the case of selected examples of polypropylene production where the propylene monomer itself acts as the diluent. Nevertheless, the diluent may mix with fluff and other components in the reactor to form a polymer slurry. In general, the diluent may facilitate circulation of the polymer slurry in the reactor, heat removal from the polymer slurry in the reactor, and so on.

The slurry discharge of the reactor typically includes the polymer fluff as well as non-polymer components such as unreacted olefin monomer (and comonomer), diluent, and so forth. This discharge stream is generally processed, such as by a diluent/monomer recovery system (e.g. flash vessel or separator vessel, purge column, etc.) to separate the non-polymer components from the polymer fluff. The recovered diluent, unreacted monomer, and other non-polymer components from the recovery system may be treated and recycled to the reactor, for example. As for the recovered polymer (solids), the polymer may be treated to deactivate residual catalyst, remove entrained or dissolved hydrocarbons, dry the polymer, and pelletize the polymer in an extruder, and so forth, before the polymer is sent to customer.

In some circumstances, to increase capacity of a polyolefin polymerization line or to achieve certain desired polymer characteristics, more than one polymerization reactor may be employed, with each reactor having its own set of conditions. In certain examples, the reactors (e.g. loop reactors) may be connected in series, such that the polymer slurry from one reactor may be transferred to a subsequent reactor, and so forth, until a polyolefin polymer is produced discharging from the final or terminal reactor with the desired set of characteristics. The respective reactor conditions including the polymerization recipe can be set and maintained such that the polyolefin (e.g., polyethylene, polypropylene) polymer product is monomodal, bimodal, or multimodal, and having polyolefin portions of different densities, and so on.

The polymerization in a single or multiple reactors is generally exothermic, or heat-generating, and is typically performed in closed systems where temperature and pressure can be regulated to control production. As with any such closed system where heat is generated, some means should be supplied to remove heat and thus to control the polymerization temperature. For loop reactors and other polymerization reactors, a cooling or coolant system is typically used to remove heat.

Variations in reactor feedstocks, utility supplies, and reaction kinetics induce variations in the reactor (polymerization) temperature which may be mitigated by the reactor temperature control scheme and the reactor coolant system. The control scheme and coolant system should also accommodate reactor upsets caused, for example, by undesirable slug feed of reactants or by rapidly changing heat transfer behavior in a fouling reactor. The production of different polyolefin products and with different reactor temperature set points may also complicate polyolefin production and its temperature control. Indeed, employment of multiple polymerization reactors in a polyolefin reactor system may add complexity in reactor temperature control and with limits in production rate, for example.

Unfortunately, with the removal of too little heat or too much heat from the reactor, such poor temperature control in the reactor increases the cost to manufacture polyolefin, such as with the economic penalty in necessitating a reduction in polyolefin production rate. Further, inadequate or inefficient reactor temperature control may result in a wider design basis for coolant system equipment and thus increases equipment costs. Furthermore, swings in reactor temperature can adversely affect the properties of the polyolefin, and also impact reactor stability leading to a reactor foul and/or unplanned shutdown, and so on.

The competitive business of polyolefin production drives manufacturers in the continuous improvement of their processes in order to improve operability and product quality, lower production costs, and so on. In an industry where billions of pounds of polyolefins are produced per year, small incremental improvements, such as in increases in polyolefin production rate, and in reducing capital and operating costs while maintaining effective temperature control and product quality, can result in a more attractive technology for licensing, and economic benefit in production including greater price margins and netback, and so forth.

SUMMARY OF THE INVENTION

An aspect of the invention relates to a polyolefin production system including: a first reactor configured to produce a first reactor discharge comprising a first polyolefin; a second reactor configured to produce a second reactor discharge comprising a second polyolefin: and a reactor transfer zone configured to receive the first reactor discharge and transfer at least a portion of the first reactor discharge to the second reactor as a second reactor transfer feed, wherein the first reactor discharge and the second reactor transfer feed have a temperature difference of at least 3° F.

Another aspect of the invention relates to a polyolefin production system including: a first reactor configured to produce a transfer slurry comprising a first polyolefin polymerized in the first reactor, a heat exchanger configured to remove heat from the transfer slurry; and a second reactor configured to receive the transfer slurry cooled by the heat exchanger, and to produce a product slurry comprising a product polyolefin having the first polyolefin and a second polyolefin polymerized in the second reactor.

Yet another aspect of the invention relates to a method of operating a polyolefin manufacturing system, including: producing a first polyolefin in a first polymerization reactor: cooling a transfer slurry comprising the first polyolefin from the first polymerization reactor; introducing the transfer slurry into a second polymerization reactor, producing a second polyolefin in the second polymerization reactor; and discharging from the second polymerization reactor a slurry comprising the first polyolefin and the second polyolefin.

Yet another aspect of the invention relates to a method of manufacturing polyolefin, including: polymerizing olefin at a first temperature in a first reactor into a first polyolefin; discharging from the first reactor a first slurry comprising the first polyolefin; cooling a feed stream; combining the feed stream with at least a portion of the first slurry to form a transfer slurry: feeding the transfer slurry to a second reactor; and polymerizing olefin at a second temperature in the second reactor into a second polyolefin, wherein the first temperature is greater than the second temperature.

BRIEF DESCRIPTION OF THE DRAWINGS

Advantages of the invention may become apparent to one of skill in the art upon reading the following detailed description and upon reference to the drawings in which.

DETAILED DESCRIPTION OF SPECIFIC EMBODIMENTS

Figure 1:
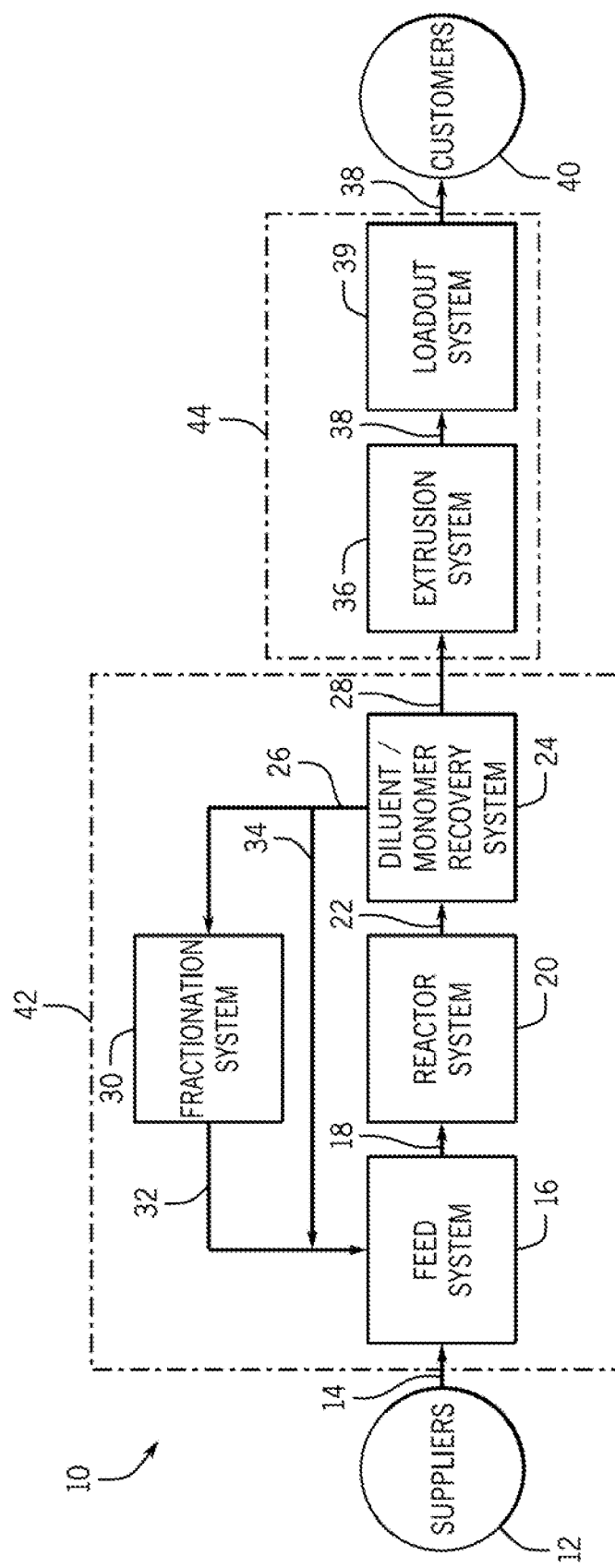
FIG. 1 is a block flow diagram depicting an exemplary polyolefin production system for producing polyolefin in accordance with embodiments of the present techniques.

One or more specific embodiments of the present invention will be described below. To provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill in the art and having the benefit of this disclosure.

The present techniques accommodate the production of the same or different polyolefins in respective polymerization reactors in series. The polyolefin produced in the reactors may be the same or different with respect to polymer density, molecular weight, and so on. To improve such production, the present techniques address temperature control of the multiple polymerization reactors in the reactor system. The techniques increase heat transfer in the downstream reactor in a multiple reactor system. Consequently, as discussed below, the production capacity may then be beneficially increased for certain heat-transfer limited resins and plants, resulting in economic benefit. While much of the heat of reaction is removed by a coolant system circulating coolant through the reactor jackets, the lowering of the temperature of the slurry transferred between the reactors facilitates additional heat-removal capability in the downstream reactor.

As for maintaining the polymerization temperature in the reactors, the cooling requirements of the respective reactors may vary considerably depending on the type or grade and amount of polyolefin being produced. In other words, the amount of heat generated in a reactor and, thus, the cooling required may be different across different grades or types and production rates of polyolefin, and between two reactors in a given reactor system, such as in bimodal production. In fact, the amount of chain transfer agent added, for example, and the degree of polymerization, may generate more or less heat of reaction. Moreover, the operating temperature setpoint of a reactor may change depending on the polyolefin being produced and, therefore, the heat-transfer dynamics may be different.

In general, to achieve desired polymer characteristics in polyolefin production, more than one polymerization reactor may be employed, with each reactor having its own set of conditions. The reactors (e.g., loop reactors) may be connected in series, such that the polymer fluff slurry from one reactor may be transferred to a subsequent reactor, and so forth, until a polyolefin polymer is produced discharging from the final or terminal reactor with the desired set of characteristics. The respective reactor conditions including the polymerization recipe can be set and maintained such that the polyolefin (e.g., polyethylene, polypropylene) polymerized in each respective reactor may have a different molecular weight, different density, and so on. In the case of two reactors in series, two polyolefin polymers (e.g., one polymerized in the first reactor and the other polymerized in the second reactor), each having a different molecular weight fraction or different density, for instance, may be combined into one polymer product discharging from the second (final) reactor.

Thus, in polyolefin production with polymerization reactors in series, the reactors can be operated to produce different polyolefin polymers in each reactor. For example, the olefin monomer may be polymerized in the first reactor to produce a high molecular-weight polyolefin and having a low or high polymer density, and the olefin monomer polymerized in the second reactor to produce a low molecular-weight polyolefin and having a low or high polymer density. On the other hand, the olefin monomer may be polymerized in the first reactor to produce a low molecular-weight polyolefin and having a low or high polymer density, and the olefin monomer polymerized in the second reactor to produce a high molecular-weight polyolefin and having a low or high polymer density. Further, similar molecular weight polyolefin may be produced in each reactor but with the polyolefin density or other properties being different in each reactor.

In a certain examples with two polymerization reactors (e.g., loop reactors) in series, a low molecular-weight high-density polyethylene (LMW HDPE) is produced in one reactor and a high molecular-weight linear low-density polyethylene (HMW LLDPE) produced in the other reactor. Thus, the combined final product is a bimodal polyethylene discharging from the final (second reactor). A chain transfer agent (e.g., hydrogen) is fed to the reactor polymerizing the LMW HDPE to terminate polymer chain growth in the addition polymerization to facilitate production of the LMW HDPE in that reactor. Therefore, as may be deduced from the foregoing discussion, the cooling requirements for the reactors may vary.

As an example of polyolefin production having a generally more demanding heat-removal requirement in the second (downstream) reactor as compared to the first reactor, is the polymerization of a low molecular weight high density (LMW-HD) component in the first reactor and a high molecular weight low density (HMW-LD) component in the second reactor. Typically, the LMW-HD component is polymerized (in the first reactor) at a higher temperature (e.g., 230° F.), and the HMW-LD component is polymerized (in the second reactor) at a lower temperature (e.g., 175° F.).

The difference in operating temperature may limit the production capability or capacity of the HMW-LD component due to reactor jacket coolant limitations. Such may be inferred, for example, by the following equations involving the logarithmic mean temperature difference (LMTD). The LMTD is defined by the logarithmic mean in the first equation (1) which is two versions of the same equation and indicates for higher reactor temperature grade products, the LMTD ($\Delta Tlm$) is greater. The polyolefin production rate and $\Delta Tlm$ may be related as shown in the second equation (2). Thus, heat removal is generally less for lower reactor temperature grade products.

$\Delta Tlm$=Coolant $\Delta T$/ln [(Reactor Temp−Inlet Coolant Temp)/(Reactor Temp−Outlet Coolant Temp)]

$\Delta Tlm$=Coolant $\Delta T$/ln [(Reactor Temp−Inlet Coolant Temp)/(Reactor Temp−Inlet Coolant Temp−Coolant $\Delta T$)]    (1)

where the Inlet Coolant Temp is the temperature of the coolant supply to the first jacket, the Outlet Coolant Temp is the temperature of the coolant return exiting the last jacket, and the Coolant $\Delta T$ is Outlet Coolant Temp minus Inlet Coolant Temp, i.e., the increase of the coolant through the reactor jackets.

(Production Rate)(Heat of Formation)=$UA\Delta Tlm$    (2)

where U is the heat transfer coefficient of the reactor jackets, A is the heat transfer area of the reactor jackets, and the Heat of Formation, for instance, is 1450 BTU/lb for polyethylene in certain examples.

The equations (1) and (2) may be employed on a design basis and operating basis. The high or maximum coolant temperature (which may be labeled as Outlet Coolant T) may be viewed as generally the greatest coolant temperature exiting the last jacket in return to the coolant system, either on a design or operating basis. The low or minimum coolant temperature (which may be labeled as Inlet Coolant T) may be viewed as the lowest temperature of the coolant from the coolant system entering the first jacket, as a design or operating basis. The Coolant $\Delta T$ is the Outlet Coolant T minus the Inlet Coolant T, either on a design or operating basis.

In certain examples for a polyolefin reactor, the Inlet Coolant Temp may be 100° F., 105° F., 110° F., 115° F., 120° F., and so on, either on a design or operating basis. The Coolant $\Delta T$ (i.e., the increase in the temperature of the coolant through the reactor jackets) may be 5° F., 7° F., 10° F., 15° F., 20° F., 25° F., 30° F., 40° F., 50° F., and so on, either on a design or operating basis. The reactor temperature control system including the reactor coolant system may be designed such that the Outlet Coolant temp, i.e., the temperature of the coolant return exiting the final jacket of the reactor returning to the coolant system, does not exceed 170° F., for example. The design and operation of the coolant system, including accounting for the coolant flow rate, for instance, may provide for a Coolant $\Delta T$ not to exceed 15° F., 25° F., 40° F., and the like.

For reactors polymerizing at lower operating temperatures, there is less temperature difference between the coolant circulating through the reactor jackets versus the contents circulating in the reactor. Thus, the driving force for heat transfer is typically less. Therefore, the heat-removal of the heat of reaction (polymerization) may be more limited in the reactor operating at a lower temperature. Further, the heat-removal must also account for removal of sensible heat in reducing the reactor temperature to the lower operating temperature set-point.

Thus, in all, in the production of a polyolefin grade with the first reactor (e.g., at 230° F.) operating at a higher temperature than the second reactor (e.g., at 175° F.), the heat transfer (removal) in the second reactor is typically more demanding. This more demanding heat-transfer in the second reactor can limit the production rate of polyolefin in the reactor system.

The present techniques may provide for an increase in the heat of reaction removal capability in the downstream reactor, which might lead to higher production rates and lower coolant system costs for the second reactor. Such an increased heat removal in the second or downstream reactor may be accomplished by increasing the overall or individual heat transfer coefficients of the reactor jackets, increasing the heat transfer area of the reactor jackets, increasing the ΔTlm by lowering the inlet coolant temperature, i.e., the low or minimum coolant temperature, the temperature of the coolant supply to the first jacket, and so forth.

As discussed in Section III below, certain embodiments to increase heat removal in the downstream reactor may provide for decreasing the temperature of streams entering the second (downstream) reactor. Such streams may include the polyolefin transfer slurry from the first (upstream) reactor, feed stream(s) such as diluent and comonomer (e.g., hexene) entering the second reactor, and so forth. Thus, these cooled streams (transfer slurry and feed stream) entering the second reactor would provide for removal of some of the heat of reaction in the second reactor, as well as absorb sensible heat from the second reactor contents (for a second reactor operating at a lower temperature than the first reactor), and the like. Such may lead to higher production rates generally and/or for certain polyolefin grades, decrease the capital and operating costs of the coolant system supplying the reactor jackets, and so on.

As discussed below in Section III, the polyolefin fluff transfer slurry from the upstream reactor may be cooled by jacketing the transfer line with a coolant such as cooling water, and/or by subjecting the transfer slurry to a plate-and-frame heat exchanger or shell-and-tube heat exchanger, or other heat removal operation. The system and operations may determine temperature ranges of the transfer slurry at the first reactor outlet and second reactor inlet, and calculate or model the additional heat of reaction that would be removed in the second reactor with the cooler incoming transfer slurry (and with cooler feed streams to the second reactor). The techniques may "convert" the increased heat removal into additional polyolefin production that might be achieved assuming no other bottlenecks, and also capture a smaller coolant system design for the second reactor since some of the heat of reaction is removed via cooler streams entering the second reactor. Again, in addition to cooling the transfer slurry, feed streams (e.g., diluent, ethylene, hexene, etc.) may be cooled to gain additional heat removal capability in the second or downstream reactor.

As for cooling the transfer slurry, the present techniques provide for reducing the temperature of the transfer slurry from the first reactor discharge by at least 3° F., 5° F., 10° F. or 20° F., and so forth. In embodiments where the second reactor is operating at a lower temperature than the first reactor, the transfer slurry may be cooled to the temperature of the second reactor, or to below (e.g., 5° F. below) the temperature of the second reactor. Thus, in a particular example where the first reactor is operating at 230° F. and the second reactor is operating at 175° F., the transfer slurry would be cooled (lowered in temperature) by 55° F. or 60° F. from 230° F. to 175° F. or 170° F., respectively.

Lastly, while the present discussion may focus on two reactors in series, the present techniques may be applicable to more than two reactors in series. Further, the techniques may apply to two or more reactors in parallel, or any combinations of series and parallel reactors. Furthermore, various combinations of molecular weights and comonomer additions in monomodal, bimodal, or multimodal polyolefin (e.g., polyethylene, polypropylene, etc.) may be applicable. Moreover, the average molecular weight of the polyolefin polymer (typically polydisperse) is herein generally referred to as "molecular weight," and sometimes as either low molecular weight (LMW) or high molecular weight (HMW) as with grades of polyolefin (e.g., polyethylene). In practice, the average molecular weight of the polyolefin may be the number average, weight average, viscosity average, z average, z+1 average, and other average characterizations.

I. Polyolefin Production Overview

Turning now to the drawings, and referring initially to FIG. 1, a block diagram depicts an exemplary production system 10 for producing polyolefin such as polyethylene, polypropylene, and their copolymers, etc. The exemplary production system 10 is typically a continuous operation but may include both continuous and batch systems. An exemplary nominal capacity for the exemplary production system 10 is about 600-1600 million pounds of polyolefin produced per year. Exemplary hourly design rates are approximately 65,000 to 200,000 pounds of polymerized/extruded polyolefin per hour. It should be emphasized, however, that the present techniques apply to polyolefin manufacturing processes including polyethylene production systems having nominal capacities and design rates outside of these exemplary ranges.

Various suppliers 12 may provide reactor feedstocks 14 to the production system 10 via pipelines, ships, trucks, cylinders, drums, and so forth. The suppliers 12 may include off-site and/or on-site facilities, including olefin plants, refineries, catalyst plants, and the like. Examples of possible feedstocks include olefin monomers and comonomers (such as ethylene, propylene, butene, hexene, octene, and decene), diluents (such as propane, isobutane, n-butane, n-hexane, and n-heptane), chain transfer agents (such as hydrogen), catalysts (such as Ziegler-Natta catalysts, chromium catalysts, and metallocene catalysts) which may be heterogeneous, homogenous, supported, unsupported, and co-catalysts such as, triethylboron, organoaluminum compounds, methyl alumninoxane (MAO), triethylaluminum (TEAl), borates, TiBAL, etc., and activators such as solid super acids, and other additives. In the case of ethylene monomer, exemplary ethylene feedstock may be supplied via pipeline at approximately 800-1450 pounds per square inch gauge (psig) at 45-65° F. Exemplary hydrogen feedstock may also be supplied via pipeline, but at approximately 900-1000 psig at 90-110° F. Of course, a variety of supply conditions may exist for ethylene, hydrogen, and other feedstocks 14.

The suppliers 12 typically provide feedstocks 14 to a reactor feed system 16, where the feedstocks 14 may be stored, such as in monomer storage and feed tanks, diluent vessels, catalyst tanks, co-catalyst cylinders and tanks, and so forth. In the case of ethylene monomer feed, the ethylene may be fed to the polymerization reactors without intermediate storage in the feed system 16 in certain embodiments. In the feed system 16, the feedstocks 14 may be treated or processed prior to their introduction as feed 18 into the polymerization reactor system 20. For example, feedstocks 14, such as monomer, comonomer, and diluent, may be sent through treatment beds (e.g., molecular sieve beds, aluminum packing, etc.) to remove catalyst poisons. Such catalyst poisons may include, for example, water, oxygen, carbon monoxide, carbon dioxide, and organic compounds containing sulfur, oxygen, or halogens. The olefin monomer and comonomers may be liquid, gaseous, or a supercritical fluid, depending on the type of reactor being fed. Also, it should be noted that typically only a relatively small amount of fresh make-up diluent as feedstock 14 is utilized, with a majority of the diluent fed to the polymerization reactor recovered from the reactor effluent.

The feed system 16 may prepare or condition other feedstocks 14, such as catalysts, for addition to the polymerization reactors. For example, a catalyst may be prepared and then mixed with diluent (e.g., isobutane or hexane) or mineral oil in catalyst preparation tanks. Further, the feed system 16 typically provides for metering and controlling the addition rate of the feedstocks 14 into the polymerization reactor to maintain the desired reactor stability and/or to achieve the desired polyolefin properties or production rate. Furthermore, in operation, the feed system 16 may also store, treat, and meter recovered reactor effluent for recycle to the reactor. Indeed, operations in the feed system 16 generally receive both feedstock 14 and recovered reactor effluent streams.

In total, the feedstocks 14 and recovered reactor effluent are processed in the feed system 16 and fed as feed streams 18 (e.g., streams of monomer, comonomer, diluent, catalysts, co-catalysts, hydrogen, additives, or combinations thereof) to the reactor system 20. As discussed below, the streams 18 may be delivered in feed conduits to the reactor which tap into the wall of the polymerization reactor in the reactor system 20. Moreover, a given feed system 16 may be dedicated to a particular reactor or to multiple reactors disposed/operated in series or parallel. Further, a feed system 16 may receive recycle components (e.g., diluent) from one or more downstream processing systems.

The reactor system 20 may have one or more reactor vessels, such as liquid-phase or gas-phase reactors. If multiple reactors are employed, the reactors may be arranged in series, in parallel, or in other combinations or configurations. Moreover, multiple reactors arranged and operated in series may be shifted in operation to a parallel or independent operation.

In the polymerization reactor vessels, one or more olefin monomers and optionally comonomers are polymerized to form a product polymer particulates, typically called fluff or granules. In one example, the monomer is ethylene and the comonomer is 1-hexene. In another example, the monomer is propylene and the comonomer is ethylene. The fluff may possess one or more melt, physical, rheological, and/or mechanical properties of interest, such as density, melt index (MI), molecular weight, copolymer or comonomer content, modulus, and the like. The reaction conditions, such as temperature, pressure, flow rate, mechanical agitation, product takeoff, component concentrations, catalyst type, polymer production rate, and so forth, may be selected to achieve the desired fluff properties.

In addition to the one or more olefin monomers and comonomers, a catalyst that facilitates polymerization of the ethylene monomer is typically added to the reactor. The catalyst may be a particle suspended in the fluid medium within the reactor. In general, Ziegler catalysts, Ziegler-Natta catalysts, metallocene catalysts, chromium catalysts, nickel catalysts, post-metallocene and other well-known polyolefin catalysts, as well as co-catalysts, may be used. Typically, an olefin-free diluent or mineral oil, for example, is used in the preparation and/or delivery of the catalyst in a feed conduit that taps into the wall of the polymerization reactor. Further, diluent may be fed into the reactor, typically a liquid-phase reactor.

The diluent may be an inert hydrocarbon that is liquid at reaction conditions, such as isobutane, propane, n-butane, n-pentane, i-pentane, neopentane, n-hexane, n-heptane, cyclohexane, cyclopentane, methylcyclopentane, ethylcyclohexane, and the like. The purpose of the diluent is generally to suspend the catalyst particles and polymer within the reactor. Diluent, as indicated, may also be used for reactor or line flushes to mitigate plugging or fouling, to facilitate flow of the polymer slurry in lines, and so on. Moreover, in examples of polypropylene production, the propylene monomer itself may act as a diluent.

A motive device may be present within each of the one or more reactors in the reactor system 20. For example, within a liquid-phase reactor, such as a loop slurry reactor, an impeller may create a mixing zone within the fluid medium. The impeller may be driven by a motor to propel the fluid medium as well as any catalyst, polyolefin fluff, or other solid particulates suspended within the fluid medium, through the closed loop of the reactor. Similarly, within a gas-phase reactor, such as a fluidized bed reactor or plug flow reactor, one or more paddles or stirrers may be used to mix the solid particles within the reactor. Lastly, the reactor system 20 typically includes a coolant system to facilitate control of temperature in the polymerization reactors.

The discharge of polyolefin fluff product slurry 22 of the reactors from system 20 may include the polymer polyolefin fluff as well as non-polymer components, such as diluent, unreacted monomer/comonomer, and residual catalyst. In construction of the reactors in certain embodiments, a discharge nozzle and conduit may be installed (e.g., welded) at a tap or hole cut into the reactor wall. The discharge of the fluff product slurry 22 exiting the reactor system (e.g., the final reactor in a series of reactors) through the discharge nozzle may be subsequently processed, such as by a diluent/monomer recovery system 24. The fluff product slurry 22 may also be called a reactor product discharge slurry, a reactor product discharge, or a reactor discharge, etc. Thus, depending on context, a "reactor discharge" may refer to the fluff slurry exiting the reactor and/or to the physical configuration (e.g., reactor wall tap or opening, nozzle, conduit, valve if any, etc.) discharging the fluff slurry.

Furthermore, it should be noted that the liquid (e.g., diluent) in fluff product slurry 22 generally partially or fully vaporizes through a flash line including a flash line heater (not shown) downstream of the reactor in route to the diluent/monomer recovery system 24. As discussed below, such vaporization may be due to decreasing pressure through the flash line, and/or due to heat added by the flash line heater (e.g., a conduit with a steam or steam condensate jacket). The diluent/monomer recovery system 24 may process the fluff product slurry 22 (whether the liquid in the slurry 22 is partially or fully vaporized in the flash line) from the reactor system 20 to separate non-polymer components 26 (e.g., diluent and unreacted monomer) from the polymer fluff 28.

A fractionation system 30 may process at least a portion of the untreated recovered non-polymer components 26 (e.g., diluent/monomer) to remove undesirable heavy and light components and to produce olefin-free diluent, for example. Fractionated product streams 32 may then return to the reactor system 20 either directly (not shown) or via the feed system 16. Such olefin-free diluent may be employed in catalyst preparation/delivery in the feed system 16 and as reactor or line flushes in the reactor system 20.

A portion or all of the non-polymer components 26 may bypass the fractionation system 30 and more directly recycle to the reactor system (not shown) or the feed system 16, as indicated by reference numeral 34. In certain embodiments, up to 80-95% of the diluent discharged from the reactor system 20 bypasses the fractionation system 30 in route to the polymerization feed system 16 (and ultimately the reactor system 20). Of course, in other embodiments, no diluent bypasses the fractionation system 30, or in other words, there is no direct recycle of diluent to the reactors. Moreover, although not illustrated, polymer granules intermediate in the recovery system 24 and typically containing active residual catalyst may be returned to the reactor system 20 for further polymerization, such as in a different type of reactor or under different reaction conditions.

The polyolefin fluff 28 discharging from the diluent/monomer recovery system 24 may be extruded into polyolefin pellets 38 in an extrusion system 36. In the extrusion system 36, the fluff 28 is typically extruded to produce polymer pellets 38 with the desired mechanical, physical, and melt characteristics. An extruder/pelletizer receives the extruder feed including one or more fluff products 28 and whatever additives have been added. Extruder feed may include additives added to the fluff products 28 to impart desired characteristics to the extruded polymer pellets 38. The extruder/pelletizer heats and melts the extruder feed which then may be extruded (e.g., via a twin screw extruder) through a pelletizer die under pressure to form polyolefin pellets 38. Such pellets are typically cooled in a water system disposed at or near the discharge of the pelletizer.

A loadout system 39 may prepare the polyolefin pellets 38 for shipment in to customers 40. In general, the polyolefin pellets 38 may be transported from the extrusion system 36 to a product loadout area 39 where the pellets 38 may be stored, blended with other pellets, and/or loaded into railcars, trucks, bags, and so forth, for distribution to customers 40. Polyolefin pellets 38 shipped to customers 40 may include low density polyethylene (LDPE), linear low density polyethylene (LLDPE), medium density polyethylene (MDPE), high density polyethylene (HDPE), enhanced polyethylene, isotactic polypropylene (iPP), syndiotactic polypropylene (sPP), including various copolymers, and so on. The polymerization and diluent recovery portions of the polyolefin production system 10 may be called the "wet" end 42 or alternatively "reaction" side of the process 10. The extrusion 36 and loadout 39 systems of the polyolefin production system 10 may be called the "dry" end 44 or alternatively "finishing" side of the polyolefin process 10. Moreover, while the polyolefin pellets 38 discharging from the extrusion system 36 may be stored and blended in the loadout area 39, the polyolefin pellets 38 are generally not altered by the loadout system 39 prior to being sent to the customer 40.

Polyolefin pellets 38 may be used in the manufacturing of a variety of products, components, household items and other items, including adhesives (e.g. hot-melt adhesive applications), electrical wire and cable, agricultural films, shrink film, stretch film, food packaging films, flexible food packaging, milk containers, frozen-food packaging, trash and can liners, grocery bags, heavy-duty sacks, plastic bottles, safety equipment, carpeting, coatings, toys and an array of containers and plastic products. To form the end-products or components, the pellets 38 are generally subjected to processing, such as blow molding, injection molding, rotational molding, blown film, cast film, extrusion (e.g., sheet extrusion, pipe and corrugated extrusion, coating/lamination extrusion, etc.), and so on. Ultimately, the products and components formed from polyolefin pellets 38 may be further processed and assembled for distribution and sale to the consumer. For example, extruded pipe or film may be packaged for distribution to the customer, or a fuel tank comprising polyethylene may be assembled into an automobile for distribution and sale to the consumer, and so on.

Process variables in the polyolefin production system 10 may be controlled automatically and/or manually via valve configurations, control systems, and so on. In general, a control system, such as a processor-based system, may facilitate management of a range of operations in the polyolefin production system 10, such as those represented in FIG. 1. Polyolefin manufacturing facilities may include a central control room or location, as well as a central control system, such as a distributed control system (DCS) and/or programmable logic controller (PLC). The reactor system 20 typically employs a processor-based system, such as a DCS, and may also employ advanced process control known in the art. The feed system 16, diluent/monomer recovery 24, and fractionation system 30 may also be controlled by the DCS. In the dry end of the plant, the extruder and/or pellet loading operations may also be controlled via a processor-based system (e.g., DCS or PLC). Moreover, in the controls systems, computer-readable media may store control executable code to be executed by associated processors including central processing units, and the like. Such code executable by the processor may include logic to facilitate the operations described herein.

The DCS and associated control system(s) in the polyolefin production system 10 may include the appropriate hardware, software logic and code, to interface with the various process equipment, control valves, conduits, instrumentation, etc., to facilitate measurement and control of process variables, to implement control schemes, to perform calculations, and so on. A variety of instrumentation known to those of ordinary skill in the art may be provided to measure process variables, such as pressure, temperature, flow rate, and so on, and to transmit a signal to the control system, where the measured data may be read by an operator and/or used as an input in various control functions. Depending on the application and other factors, indication of the process variables may be read locally or remotely by an operator, and used for a variety of control purposes via the control system.

A polyolefin manufacturing facility typically has a control room from which the plant manager, engineer, technician, supervisor and/or operator, and so on, monitors and controls the process. When using a DCS, the control room may be the center of activity, facilitating the effective monitoring and control of the process or facility. The control room and DCS may contain a Human Machine Interface (HMI), which is a computer, for example, that runs specialized software to provide a user-interface for the control system. The HMI may vary by vendor and present the user with a graphical version of the remote process. There may be multiple HMI consoles or workstations, with varying degrees of access to data.

II. Polymerization Reactor System

As discussed above, the reactor system 20 may include one or more polymerization reactors, which may in turn be of the same or different types. Furthermore, with multiple reactors, the reactors may be arranged serially or in parallel. Whatever the reactor types in the reactor system 20, a polyolefin particulate product, generically referred to as "fluff" herein, is produced. To facilitate explanation, the following examples are limited in scope to specific reactor types believed to be familiar to those skilled in the art and to combinations. To one of ordinary skill in the art using this disclosure, however, the present techniques are applicable to more complex reactor arrangements, such as those involving additional reactors, different reactor types, and/or alternative ordering of the reactors or reactor types, as well as various diluent and monomer recovery systems and equipment disposed between or among the reactors, and so on. Such arrangements are considered to be well within the scope of the present invention.

One reactor type include reactors within which polymerization occurs within a liquid phase. Examples of such liquid phase reactors include autoclaves, boiling liquid-pool reactors, loop slurry reactors (vertical or horizontal), and so forth. For simplicity, a loop slurry reactor which produces polyolefin, such as polyethylene or polypropylene, is discussed in the present context though it is to be understood that the present techniques may be similarly applicable to other types of liquid phase reactors.

Figure 2:
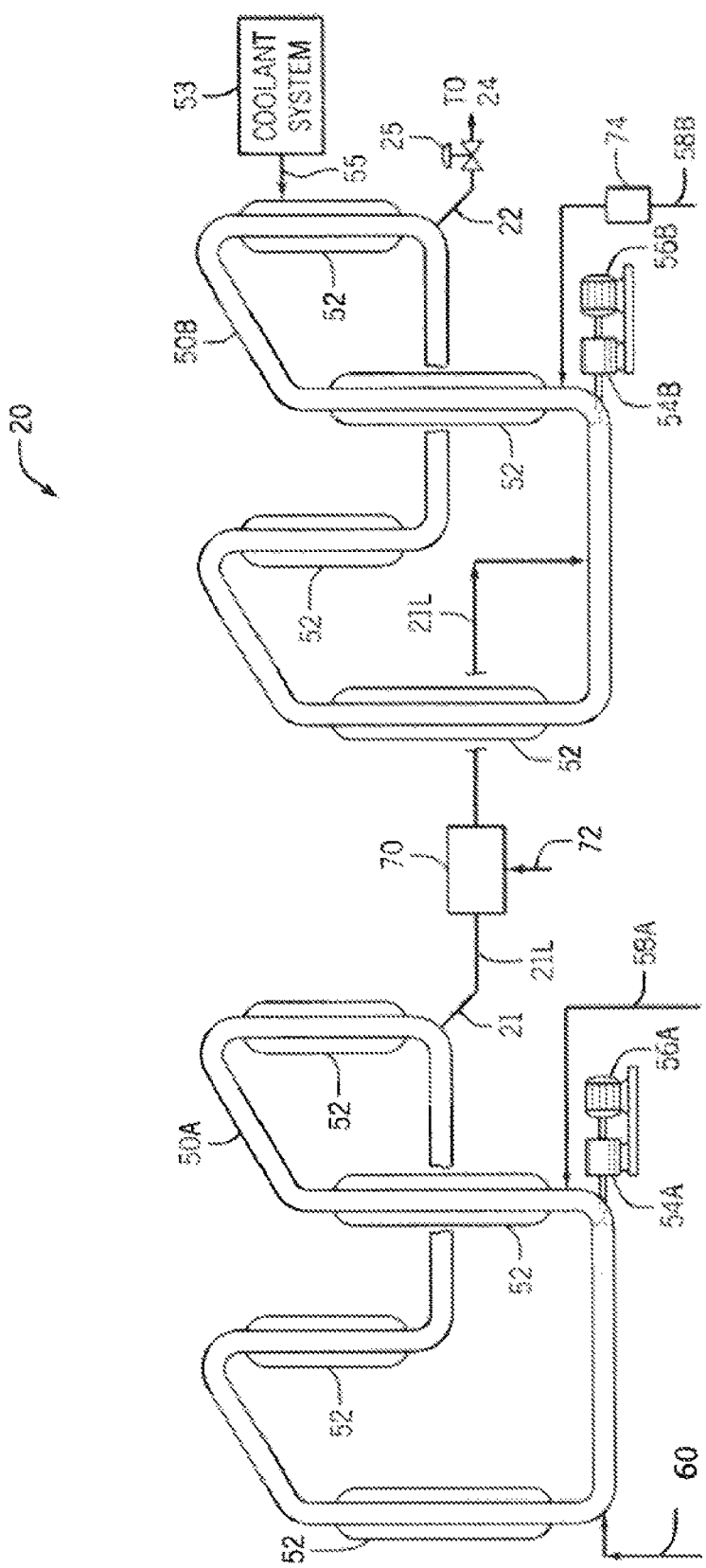
FIG. 2 is a process flow diagram of an exemplary reactor system of the polyolefin production system of FIG. 1 in accordance with embodiments of the present techniques.

FIG. 2 depicts an exemplary polymerization reactor system 20 (of FIG. 1) as having two loop slurry (polymerization) reactors 50A, 50B disposed and operated in series. Additional loop reactors or other reactors (e.g., autoclave reactors, gas phase reactors, etc.) may be disposed in series or parallel in the illustrated combination. Moreover, in embodiments, the reactors 50A, 50B may be shifted to a parallel operation. The present techniques contemplate aspects of a variety of reactor system configurations such as those also disclosed in U.S. Patent Application Publication No. 2011/0288247 which is incorporated by reference herein in its entirety.

Processing equipment may be disposed between the two loop reactors 50A, 50B, and so on. The processing equipment disposed between the reactors 50A, 50B, if so disposed, may remove diluent, solids, light components, ethane, hydrogen, and so forth, from the transfer slurry 21 for recycle to the first reactor 50A and/or to a recovery system, and the like. This processing disposed between the reactors may also have capability, as discussed below in Section III to remove heat from and lower the temperature of the transfer slurry discharging from the first reactor to the second reactor.

A loop slurry reactor 50A, 50B is generally composed of segments of pipe connected by smooth bends or elbows. The representation of the loop reactors 50A, 50B in FIG. 2 is simplified, as appreciated by the skilled artisan. Indeed, an exemplary reactor 50A, 50B configuration may include eight to sixteen or other number of jacketed vertical pipe legs approximately 24 inches in diameter and approximately 200 feet in length, connected by pipe elbows at the top and bottom of the legs. FIG. 2 shows a four leg segment reactor arranged vertically. It could also be arranged horizontally.

The reactor jackets 52 are normally provided to remove heat from the exothermic polymerization via circulation of a cooling medium or coolants, such as treated water, through the reactor jackets 52. In the illustrated embodiment, a coolant system 53 provides coolant supply 55 to the reactor jackets 52. The coolant system 53 may receive a coolant return from the reactor jackets 52.

As discussed above in certain examples for a polyolefin reactor, the inlet coolant temperature, the minimum or low coolant temperature, or the coolant supply 55 temperature to the reactor jackets 52 may be 100° F., 105° F., 110° F., 115° F., 120° F., and so on. The coolant ΔT or increase in the temperature of the coolant through the reactor jackets 52 may be 5° F., 7° F., 10° F., 15° F., 20° F., 25° F., 30° F., 40° F., 50° F., and so on. The reactor temperature control system including the reactor coolant system 53 may be designed such that the temperature of the coolant return exiting the final jacket 52 of the reactor returning to the coolant system 53 does not exceed 170° F., for example. The design (including the coolant flow rate, for instance) may provide for a maximum or high coolant ΔT through the jackets 52 of 15° F., 25° F., 40° F., and the like.

The present techniques may provide for an increase in the heat of reaction removal capability in the downstream reactor 50B, which might lead to higher production rates and lower coolant system costs for the second reactor. Such an increased heat removal in the second or downstream reactor 50B may be accomplished by increasing the overall or individual heat transfer coefficients of the reactor jackets 52, increasing the heat transfer area of the reactor jackets 52, and so forth. Additional heat removal may involve increasing the ΔTlm by lowering the inlet coolant temperature (minimum or low coolant temperature) from the coolant system to the first jacket 52, i.e., lowering the temperature of the coolant supply 55 discharging from the coolant system 53. The transfer slurry 21 and feed 58B may also be cooled to increase heat removal capability in the second reactor 50B.

The reactors 50A, 50B may be used to carry out polyolefin (e.g., polyethylene, polypropylene) polymerization under slurry conditions in which insoluble particles of polyolefin are formed in a fluid medium and are suspended as slurry until removed. A respective motive device, such as pump 54A, 54B, circulates the fluid slurry in each reactor 50A, 50B. An example of a pump 54A, 54B is an in-line axial flow pump with the pump impeller disposed within the interior of the reactor 50A, 50B to create a turbulent mixing zone within the fluid medium. The impeller may also assist in propelling the fluid medium through the closed loop of the reactor at sufficient speed to keep solid particulates, such as the catalyst or polyolefin product, suspended within the fluid medium. The impeller may be driven by a motor 56A, 56B or other motive force.

The fluid medium within each reactor 50A, 50B may include olefin monomers and comonomers, diluent, co-catalysts (e.g., alkyls, triethylboron, TiBAL, TEAl, methyl aluminoxane or MAO, borates, TEB, etc.), activator supports like solid super acids, molecular weight control agents (e.g., hydrogen), and any other desired co-reactants or additives. Such olefin monomers and comonomers are generally 1-olefins having up to 10 carbon atoms per molecule and typically no branching nearer the double bond than the 4-position. Examples of monomers and comonomers include ethylene, propylene, butene, 1-pentene, 1-hexene, 1-octene, and 1-decene. Again, typical diluents are hydrocarbons which are inert and liquid under reaction conditions, and include, for example, isobutane, propane, n-butane, n-pentane, i-pentane, neopentane, n-hexane, n-heptane, cyclohexane, cyclopentane, methylcyclopentane, ethylcyclohexane, and the like. These components are added to the reactor interior via inlets or conduits at specified locations, such as depicted at feed streams 58A, 58B, which generally corresponds to one of the feed streams 18 of FIG. 1.

Likewise, a catalyst, such as those previously discussed, may be added to the reactor 50A via a conduit at a suitable location, such as depicted at feed stream 60, which may include a diluent carrier and which also generally corresponds to one of the feed streams 18 of FIG. 1. Again, the conduits that feed the various components tie-in (i.e., flange or weld) to the reactor 50. In the illustrated embodiment, catalyst feed 60 is added to the first reactor 50A in series but not to the second reactor SOB. However, active catalyst may discharge in a fluff slurry 21 from the first reactor 50A to the second reactor SOB. Moreover, while not depicted, a fresh catalyst may be added to the second reactor 50B in certain embodiments. In total, the added components including the catalyst and other feed components generally compose a fluid medium within the reactor 50A, 50B in which the catalyst is a suspended particle. Lastly, as discussed below in Section III, the diluent and monomer added (e.g. as stream 58B) to the second reactor 50B may be cooled in certain instances to facilitate temperature control of the second reactor 50B.

The reaction conditions, such as temperature, pressure, and reactant concentrations, in each reactor 50A, 50B are regulated to facilitate the desired properties and production rate of the polyolefin in the reactor, to control stability of the reactor, and the like. Temperature is typically maintained below that level at which the polymer product would significantly go into solution, swell, soften, or become sticky. As indicated, due to the exothermic nature of the polymerization reaction, a cooling fluid or coolant may be circulated through jackets 52 around portions of the loop slurry reactor 50A, 50B to remove excess heat, thereby maintaining the temperature within the desired range, generally between 150° F. to 250° F. (65° C. to 121° C.). Likewise, pressure in each loop reactor 50A, 50B may be regulated within a desired pressure range, generally 100 to 800 psig, with a range of 450 to 700 psig being typical. Of course, the reactor cooling and temperature control techniques disclosed herein may be applicable to lower-pressure polyolefin processes, such as those with reactors operating in a typical range of 50 psig to 100 psig, and with hexane as a common diluent, for example.

As the polymerization reaction proceeds within each reactor 50A, 50B, the monomer (e.g., ethylene) and comonomers (e.g., 1-hexene) polymerize to form polyolefin (e.g., polyethylene) polymers that are substantially insoluble in the fluid medium at the reaction temperature, thereby forming a slurry of solid particulates within the medium. These solid polyolefin particulates may be removed from each reactor 50A, 50B via a reactor discharge. In the illustrated embodiment of FIG. 2, a transfer slurry 21 is discharged from the first reactor 50A, and a product slurry 22 is discharged from the second reactor 50B.

For the transfer slurry 21 and product slurry 22, respectively, each reactor discharge may be (1) an intermittent discharge such as a settling leg, pulsating on/off valve, and so on, or (2) a continuous discharge such as continuous take-off (CTO) which optionally has a modulating valve, and so forth. Further, the discharges may be subjecting to processing (not illustrated) such as pumping (i.e., via a pump), heating, cooling, evaporative cooling, separation such as with a hydrocyclone or other separation device/vessel, and so on. As for a continuous discharge, a variety of discharge configurations are contemplated. For instance, employment of an isolation valve (e.g., full-bore Ram valve) without an accompanying modulating valve may provide for continuous discharge of slurry from the loop reactor. Further, a CTO is defined as having at least a modulating flow valve, and provides for a continuous discharge of slurry from the loop reactor. In certain examples, a CTO is further defined as a continuous discharge having a modulating valve (e.g., v-ball valve) on the discharge conduit at the reactor and an isolation valve (e.g., Ram valve) at the reactor wall. It should be noted that a Ram valve in a closed position may beneficially provide a surface that is flush with the inner wall of the reactor to preclude the presence of a cavity, space, or void for polymer to collect when the Ram valve is in the closed position.

As for a continuous discharge of the transfer slurry 21 from the first reactor 50A, a continuous discharge on the first reactor may be a CTO (not shown), or may be a continuous discharge (as shown) without a modulating valve (but with an isolation valve, for example), and so on. Moreover, the reactors could be run at the same or different pressures. The continuous transfer without a modulating valve could better take advantage of the pressure drop in the reactor for the driving force for transfer. The available motive force for transfer of a discharge slurry 21 may be considered as the pressure drop (i.e., from the discharge of the pump 54A to the suction of the pump 54B) through the first reactor 50A.

The pressure differential between the discharge of the first loop reactor pump 54A and the suction of the second loop reactor pump 54B may provide a motive force for the transfer of transfer slurry 21 from the first loop reactor 50A to the second loop reactor 50B. The pump suction, whether of the first pump 54A or second pump 54B, may be considered upstream of the pump (from the pump inlet) in pipe length of the respective loop in the range of up to about 0.5 meter to 50 meters (e.g., 0.5, 1, 5, 15, 25, 50 meters, or values in between). Similarly, the pump discharge may be considered a pipe length from the pump outlet up to about 0.5 meter to 50 meters (e.g., 0.5, 1, 5, 15, 25, 50 meters, or values in between), as well up to 100 meter, and more. The actual motive force realized for the transfer slurry 21 may depend on the location of the first reactor 50A discharge into the transfer line 21L relative to the pump 54A) and the location on the second loop reactor 50B (relative to the pump 54B) of the other end of the transfer line 21L. The location for the transfer line 21L relative to the pumps 54A and 54B may be selected to give adequate motive force (delta P) for flow of the transfer slurry 21 through the transfer line 21L. i.e., to overcome the hydraulic resistance or pressure losses (drop) through the transfer line 21L (as well as through any additional processing equipment such as a hydrocyclone, evaporation cooler, etc.) to the second reactor 50B. Moreover, in certain embodiments, a pump (not shown) may further provide motive force and facilitate movement of the transfer slurry 21 to the second reactor 50B.

Again, in certain examples, the two loop reactors 50A, 50B may be operated in series and such that the polyolefin fluff in the fluff slurry 22 discharging from the second reactor 50B is monomodal or bimodal. In certain cases of monomodal production, the reactor operating conditions may be set such that essentially the same polyolefin or similar polyolefin is polymerized in each reactor 50A, 50B. On the other hand, in monomodal production in terms of molecular weight, the conditions in the reactor may be the same or similar such as with regard to hydrogen concentration but different in terms of comonomer concentration, for example, so to produce polyolefin with similar molecular weight but different polymer density in each reactor.

In the case of bimodal production, the reactor operating conditions may be set such that the polyolefin polymerized in the first reactor 50A is different than the polyolefin polymerized in the second reactor 50B. Thus, with two reactors, a first polyolefin produced in the first loop reactor 50A and the second polyolefin produced in the second loop reactor SOB may combine to give a bimodal polyolefin or a monomodal polyolefin. Further, again, whether monomodal or bimodal, i.e. in terms of molecular weight, the first polyolefin produced in the first loop reactor 50A and the second polyolefin produced in the second loop reactor 50A may have different polymer densities, for example.

Operation of the two loop reactors 50A, 50B may include feeding more comonomer to the first polymerization reactor than to the second polymerization rector, or vice versa. The operation may also include feeding more chain transfer agent (e.g., hydrogen) to the second polymerization reactor than the second reactor, or vice versa. Of course, the same amount of comonomer and/or the same amount of chain transfer agent (e.g., hydrogen) may be fed to each reactor 50A, 50B. Further, the same or different comonomer concentration may be maintained in each reactor 50A, 50B. Likewise, the same or different chain transfer agent (e.g., hydrogen) concentration may be maintained in each reactor 50A, 50B.

Furthermore, the first polyolefin (i.e., polyolefin polymerized in the first reactor 50A) may have a first range for a physical property, and the second polyolefin (i.e., polyolefin polymerized in the second reactor 50B) may have a second range for the physical property. The first range and the second range may be the same or different. Exemplary physical properties may include polyolefin density, comonomer percentage, short chain branching amount, molecular weight, viscosity, melt index, melt flow rate, crystallinity, and the like. Moreover, as discussed below, the cooling requirements in the respective reactors 50A, 50B may be different, depending on the polyolefin polymerized and polymerization condition in the respective reactors 50A, 50B.

As indicated, the polyolefin product fluff slurry 22 discharges from the second reactor 50B and is subjected to downstream processing, such as in a diluent/monomer recovery system 24. As mentioned, the product fluff slurry 22 may discharge through a settling leg, a continuous take-off (CTO), or other valve configurations. Indeed, the product fluff slurry 22 may discharge intermittently such as through a settling leg configuration or pulsating on/off valve, or instead may discharge continuously such as through a CTO. In the illustrated embodiment of FIG. 2, a CTO having a modulating valve 25 is employed for the product fluff slurry 22 discharging from the second reactor 50B.

In operation, depending on the positioning, for example, of the discharge on the second reactor, a discharge slurry 22 having a greater solids concentration than the slurry circulating in the reactor 50B may be realized with continuous discharge. Again, a continuous discharge may include a discharge configuration having an isolation valve (Ram valve) alone, or having a CTO configuration with an isolation valve (Ram valve) and modulating valve 25. Exemplary CTO configurations and control, and other discharge configurations, may be found in the aforementioned U.S. Patent Application Publication No. 2011/0288247, and in U.S. Pat. No. 6,239,235 which is also incorporated herein by reference in its entirety.

As mentioned, in the illustrated embodiment, the product fluff slurry 22 discharges through a CTO. In certain examples, a CTO has a Ram valve at the reactor 50B wall, and a modulating flow control valve 25 (e.g., v-ball control valve) on the discharge conduit. However as indicated, in an alternate embodiment, the product fluff slurry 22 may discharge through a settling leg configuration, for example, in lieu of a CTO.

In the embodiment of FIG. 2, a transfer fluff slurry 21 discharges from the first loop reactor 50A to the second loop reactor 50B via a transfer line 21L. The contents of transfer fluff slurry 21 may be representative of the contents of the first loop reactor 50A. However, the solids concentration may be greater in the transfer slurry 21 than in the first loop reactor 50A, depending on the positioning of the inlet of the transfer line 21L on the first loop reactor 50A, for example, and other considerations. The transfer fluff slurry 21 may discharge from the first loop reactor 50A into the transfer line 21L through a settling leg, an isolation valve (e.g., a Ram valve), a continuous take-off CTO (which as indicated the CTO has both an isolation Ram valve and a modulating valve), or other valve configuration.

In the illustrated embodiment, the discharge of the transfer slurry 21 from the first loop reactor 50A is continuous and not directly modulated. A CTO or settling leg is not employed. Instead, the transfer slurry 21 discharges through an isolation valve (e.g., Ram valve) (not shown) at the reactor wall and without a modulating valve on the transfer line 21L in this example. In a particular example, the transfer slurry 21 discharges through a full-bore Ram valve maintained in a full-open position, and not additionally through a modulating valve. In alternate embodiments (not illustrated), a modulating valve may be disposed downstream on the transfer line 21, or a CTO with its modulating valve may be situated at the transfer slurry 21 discharge of the first reactor 50A. If so included, the modulating valve may control flow rate of the transfer slurry 21 and facilitate control of pressure in the first loop reactor 50A. Moreover, a modulating valve or a CTO and its modulating valve may be disposed to facilitate control of the first reactor 50A discharge when the two reactors 50A and 50B are shifted in operation to parallel performance, for instance.

Nevertheless, in the various embodiments, an isolation (e.g., Ram) valve is typically disposed on the discharge at the wall of the first loop reactor 50A. The Ram valve may provide for isolation of the transfer line 21L from the loop reactor 50A when such isolation is desired. A Ram valve may also be positioned at the outlet of the transfer line 21L at the wall of the second loop reactor SOB to provide for isolation of the transfer line 21L from the second loop reactor SOB when such isolation is desired. It may be desired to isolate the transfer line 21L from the first and second loop reactors 50A, 50B during maintenance or downtime of the reactor system 20, or when an alternate discharge or transfer line from the first reactor 50A is placed in service, and so on. The operation or control of the Ram valves may be manual, hydraulic-assisted, air-assisted, remote, automated, and so on. The transfer line 21L may be manually removed from service (e.g., manually closing the Ram valves) or automatically removed (e.g., via a control system automatically closing the Ram valves) from service.

In the illustrated embodiment, control of pressure (and throughput) in the first loop reactor 50A and the second loop reactor 50B may be facilitated by operation of the CTO flow control valve 25. In some examples, the pressure in the first loop reactor 50A may float on the pressure in the second loop reactor 50B. The reactors 50A, 50B may be maintained at the same, similar, or different pressure. Pressure elements or instruments may be disposed on the reactors 50A, 50B and on the transfer line 21L. Further, other process variable elements or instruments indicating temperature, flow rate, slurry density, and so forth, may also be so disposed.

Such instrumentation may include a sensor or sensing element, a transmitter, and so forth. For a pressure element, the sensing element may include a diaphragm, for example. For a temperature element or instrument, the sensing element may include a thermocouple, a resistance temperature detector (RTD), and the like, of which may be housed in a thermowell, for instance. Transmitters may convert a received analog signal from the sensing element to a digital signal for feed or transmission to a control system, for example. The various instruments may have local indication of the sense variable. For instance, a pressure element or instrument may be or have a local pressure gauge and a temperature element or instrument may be or have a local temperature gauge, both of which may be read locally by an operator or engineer, for example.

The inlet position of the transfer line 21L may couple to the first loop reactor 50A on the discharge side of the circulation pump 56A in the first loop reactor 50A. The outlet position of the transfer line 21L may couple to the second loop reactor on the suction side of the circulation pump 56B in the second loop reactor 50B. Such a configuration may provide a positive pressure differential (i.e., a driving force) for flow of transfer slurry 21 through the transfer line 21L from the first loop reactor 50A to the second loop reactor 50B. In one example, a typical pressure differential (provided from the discharge of the first pump 54A to the suction of the second pump 54B) is about 20 pounds per square inch (psi). Again, the pump suction side, whether of the first pump 54A or second pump 54B, may be considered upstream of the pump in linear loop pipe length in the range of about 0.5 meter to 50 meters (e.g., 0.5, 1, 5, 15, 25, 50 meters, or values therebetween). Similarly, the pump discharge side may be considered downstream of the pump in linear loop pipe length of about 0.5 meter to 50 meters (e.g., 0.5, 1, 5, 15, 25, 50 meters, or values therebetween), and up to about 100 meters, and so on.

III. Cooling of Transfer Slurry Between Reactors

As depicted in FIG. 2, a heat-removal apparatus 70 removes heat from the transfer slurry 21. The cooling medium 72 may be cooling tower water, treated water, refrigerant, or other cooling medium. In certain embodiment, the cooling medium 72 may also be coolant from the cooling system 53, i.e., the same or similar as the coolant 55 supplied to the reactor jackets 52. It should be noted that in alternate embodiments (not illustrated), a portion of the transfer slurry 21 may be processed (such as through a hydrocyclone) and recycled including returned to the first reactor, and thus in certain embodiments only a portion of the slurry discharged from the first reactor 50A is cooled as the transfer slurry 21 in the heat-removal apparatus 70 to the second reactor 50B.

The depicted heat-removal apparatus 70 may represent a jacket heat exchanger around the transfer line 21L. Such a jacket may be an external conduit or pipe surrounding the transfer line 21L (e.g., which is also a conduit or pipe) to form an annulus in which a cooling medium 72 may flow. In other examples, the heat-removal apparatus 70 may include other types of heat exchangers, such as a plate-and-frame heat exchanger, a shell-and-tube heat exchanger, and so forth. In sum, the heat-removal apparatus 70 may be one or more heat exchangers, and may include a jacketed pipe heat exchanger, a shell-and-tube heat exchanger, or a plate-and-frame heat exchanger, or any combination thereof. Of course, the heat-removal apparatus 70 may be other kinds of heat exchanger or heat-removal devices. For instance, the apparatus 70 may incorporate evaporative or evaporation cooling which may involve flashing diluent, for instance, in the transfer slurry. Moreover, a pump external to or a component of the heat-removal apparatus 70 may facilitate transfer of the cooled transfer slurry 21.

The heat-removal apparatus 70 may include a vessel and piping to provide for evaporation cooling. In certain examples, diluent and other liquid components in the transfer slurry 21 may be flashed in the vessel and recovered, to give cooling of transfer slurry 21 sent to the second reactor.

Further, as indicated, one or more of the feed streams 58B to the second reactor 50B may be cooled such as with a heat-removal apparatus 74. The feed streams 58B may include diluent (e.g., isobutane), monomer (e.g., ethylene or propylene), and comonomer (e.g., 1-hexene), and the like. As with the cooling between reactors, the cooling medium to the additional heat-removal apparatus 74 for the feed streams 58B may include cooling tower water, treated water, refrigerant, or other cooling medium. In certain embodiments, the cooling medium to the heat-removal apparatus 74 may be or include coolant from the cooling system 53. Moreover, it should be noted that a optionally cooled feed stream, such as one or more of the feed streams 58B or other feed streams optionally subjected to cooling may be combined with the transfer slurry 21 or portion of the transfer slurry 21 to give a cooled transfer slurry 21 fed to the second reactor 50B. The cooled feed stream and the transfer slurry 21 may have a temperature difference of at least 3° F., 5° F., 10° F., 15° F., 20° F., or more.

Lastly, it should be noted that the first reactor 50A and the second reactor 50B may have a first to second reactor capacity ratio of between 0.5:1 and 1.5:1, for example. In other words, the polyolefin production ratio between the two reactors may be varied from 0.5 to 1.5 as theoretical or practical limits in certain examples. In some instances, the lower 0.5 indicates the turn down capability and the upper 1.5 may be an upper design limit. In other examples, the polyolefin production ratio is 0.5 to 1.3. Moreover, the first reactor and the second reactor may be substantially the same size in volume (or capacity), or differ in size by volume (or capacity). In certain examples, the first reactor is 50% to 90% in size by volume (or capacity) of the second reactor and, therefore, the polyolefin production contribution of the first reactor would typically be less than the polyolefin production contribution of the second reactor. In other examples, the second reactor is 50% to 90% in size by volume (or capacity) of the first reactor and, therefore, the polyolefin production contribution of the second reactor would typically be less than the polyolefin production contribution of the first reactor.

Figure 3:
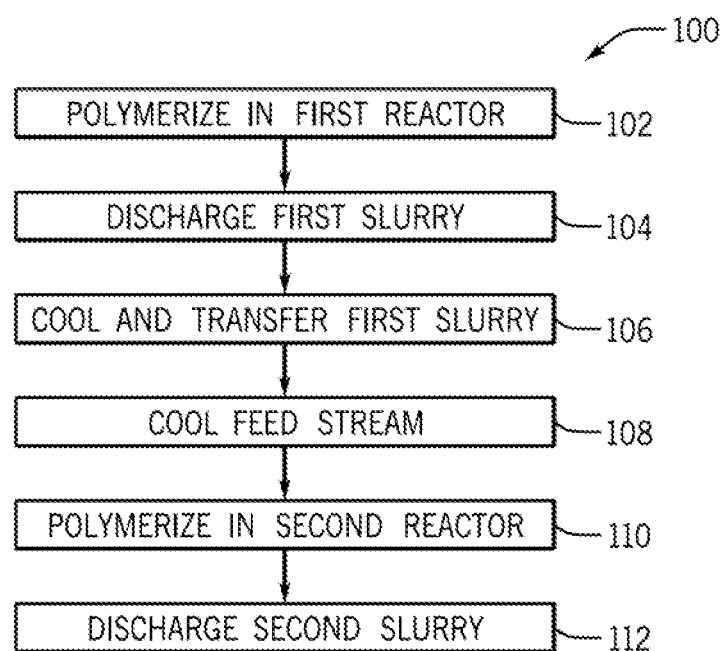
FIG. 3 is a block diagram of an exemplary method of manufacturing polyolefin in accordance with embodiments of the present techniques.

FIG. 3 is a method 100 of manufacturing a polyolefin, of operating a polyolefin manufacturing system. While the method 100 may be beneficial generally, the illustrated method may be beneficial in particular where the second reactor is operated at a lower temperature than the first reactor in a reactor system having two reactors in series.

In the method 100, a first polyolefin is produced in a first polymerization reactor. For instance, an olefin is polymerized (block 102) in the first reactor to produce the first polyolefin. A first slurry having the first polyolefin is discharged (block 104) from the first reactor. The first slurry or at least a portion of the first slurry is cooled (block 106), such as with a heat exchanger and/or via evaporation cooling. For example, the first slurry (or a portion of the first) may be routed as a transfer slurry through a heat exchanger, and heat removed and absorbed by a cooling medium in the heat exchanger. The cooled first slurry or cooled portion of the first slurry may be routed or transferred (block 106) as a transfer slurry to a second reactor. Optionally, a feed stream to the second reactor may also be cooled (108), such as via an additional heat exchanger. Such a cooled feed stream may be fed directly to the second reactor or combined with the transfer slurry in route to the second reactor.

A second polyolefin is produced in the second polymerization reactor. For instance, an olefin is polymerized (block 110) in the second reactor to produce the second polyolefin. In certain embodiments, a combined or product polyolefin may form in the second reactor and having the first polyolefin and the second polyolefin. The product polyolefin may be a bimodal polyolefin, for example, with the first polyolefin and second polyolefin having different molecular weights. A second slurry (e.g., product slurry) is discharged (block 112) from the second reactor. The second slurry may be subjected to additional processing. The product polyolefin ultimately pelletized into product polyolefin pellets for distribution to customers.

IV. Summary

Embodiments of the present techniques provide for a polyolefin production system including: a first reactor configured to produce a first reactor discharge having a first polyolefin: a second reactor configured to produce a second reactor discharge having a second polyolefin; and a reactor transfer zone configured to receive the first reactor discharge and transfer at least a portion of the first reactor discharge to the second reactor as a second reactor transfer feed, wherein the first reactor discharge and the second reactor transfer feed have a temperature difference of at least 3° F., 5° F., 10° F. or 20° F. The reactor transfer zone may be configured to receive a cooling medium to remove heat from the second reactor transfer feed. The reactor transfer zone may include a heat exchanger. The reactor transfer zone may include a slurry transfer line for the second reactor transfer feed, the slurry transfer line having a jacket for a cooling medium. The reactor transfer zone may include a vessel configured for evaporative cooling (e.g., of the first reactor discharge or the second reactor transfer feed) to lower the temperature of the second reactor transfer feed. In certain examples, diluent and other liquid components in the second reactor transfer feed may be flashed in the vessel and recovered, to give cooling of the remaining second reactor transfer feed sent to the second reactor. In some embodiments, the first polyolefin is a low molecular weight—high density polyolefin, and the second polyolefin is a high molecular weight-low density polyolefin. Lastly, the first and second reactors may have a first to second reactor production rate ratio in the range of 0.5:1 to 1.5:1, or in the range of 0.5:1 to 1.3:1.

Embodiments provide for a polyolefin production system including: a first reactor configured to produce a transfer slurry comprising a first polyolefin polymerized in the first reactor; a heat exchanger configured to remove heat from the transfer slurry; and a second reactor configured to receive the transfer slurry cooled by the heat exchanger, and to produce a product slurry comprising a product polyolefin having the first polyolefin and a second polyolefin polymerized in the second reactor. The heal exchanger may be configured to receive a cooling medium, and wherein the heat exchanger may be a jacketed pipe heat exchanger, a shell-and-tube heat exchanger, or a plate-and-frame heat exchanger, or any combination thereof. The system may include a transfer line to route the transfer slurry to the second reactor, wherein the heat exchanger is disposed along the transfer line. As indicated, in certain examples, the first polyolefin is a low molecular weight-high density polyolefin, and the second polyolefin is a high molecular weight-low density polyolefin. An additional heat exchanger may be employed to remove heat from a feed stream to the second reactor. Such a feed stream may be a diluent feed stream and/or a feed stream having monomer or comonomer, or both, and the like.

The techniques may provide for a polyolefin production system including: a first polymerization reactor configured to produce a first polyolefin and discharge a first slurry comprising the first polyolefin, wherein at least a portion of the first slurry is a transfer slurry; a heat exchanger configured to remove heat from the transfer slurry, and a second polymerization reactor configured to receive the transfer slurry cooled by the heat exchanger, produce a second polyolefin, and discharge a second slurry comprising a product polyolefin a having the first polyolefin and the second polyolefin. The product polyolefin may be bimodal. The polyolefin could be multimodal with at least 2 MW peaks. On the other hand, the MW of the product polyolefin could be broad with no appreciable MW peak, or where MW peak(s) need to be deconvoluted, and so on. In many examples, the heat exchanger has an inlet for a cooling medium. The heat exchanger may be one or more heat exchangers, and may include a jacketed pipe heat exchanger, a shell-and-tube heat exchanger, or a plate-and-frame heat exchanger, or any combination thereof.

Certain embodiments of the present techniques provide for a polymerization reactor system including: a first polyolefin reactor configured to produce a first polyolefin and discharge an intermediate slurry comprising the first polyolefin; a transfer line configured to route and introduce at least a portion of the intermediate slurry to a second polyolefin reactor; the second polyolefin reactor configured to produce a second polyolefin and discharge a product slurry comprising the first polyolefin and the second polyolefin; and a heat exchanger disposed along the transfer line and configured to remove heat from the at least a portion of the intermediate slurry transfer slurry in the transfer line. The heat exchanger may generally have an inlet to receive a cooling medium.

Other embodiments provide a method of operating a polyolefin manufacturing system, including: producing a first polyolefin in a first polymerization reactor; cooling a transfer slurry having first polyolefin from the first polymerization reactor: introducing the transfer slurry into a second polymerization reactor; producing a second polyolefin in the second polymerization reactor, and discharging from the second polymerization reactor a slurry comprising the first polyolefin and the second polyolefin. Cooling the transfer slurry generally includes receiving a cooling medium to cool the transfer slurry. For instance, a cooling medium may be received at a heat exchanger (e.g., a shell-and-tube heat exchanger or to a plate-and-frame heat exchanger, or to both), and the transfer slurry subjected to the heat exchanger to cool the transfer slurry. The transfer slurry may be through a conduit jacketed with a cooling medium. In particular, for example, the transfer slurry may be routed through a transfer line having a pipe jacket with a cooling medium in the pipe jacket.

The transfer slurry may be routed through a first portion of a transfer line to a heat exchanger, and wherein cooling the transfer slurry is accomplished by removing heat from the transfer slurry via the heat exchanger. The cooled transfer slurry may be then routed through a second portion of the transfer line from the heat exchanger to the second reactor. Moreover, the cooling of the transfer slurry may include evaporative or evaporation cooling of the transfer slurry. The evaporative or evaporation cooling may involve flashing diluent, for instance, in the transfer slurry.

It should be noted that producing the first polyolefin may involve polymerizing olefin at a first temperature in the first polymerization reactor. Producing the second polyolefin may involve polymerizing olefin at a second temperature in the second polymerization reactor, wherein the first temperature is greater than the second temperature. The slurry discharged from the second polymerization reactor may include a product polyolefin (e.g., bimodal polyolefin) having the first polyolefin (e.g., high density) and the second polyolefin (e.g., low density). The method may include pelletizing the product polyolefin to form product polyolefin pellets.

Embodiments may also include a method of manufacturing polyolefin, including: polymerizing olefin at a first temperature in a first reactor into a first polyolefin; discharging from the first reactor a first slurry having the first polyolefin; transferring at least a portion of the first slurry as a transfer slurry to a second reactor: removing heat from the first slurry or from the transfer slurry in route to the second reactor; polymerizing olefin at a second temperature in the second reactor into a second polyolefin, wherein the first temperature is greater than the second temperature; and discharging from the second reactor a slurry having the first polyolefin and the second polyolefin. The method may also include cooling a feed stream to the second reactor. Moreover, the first reactor and the second reactor may substantially the same size in volume, or differ in site by volume. In certain examples, the first reactor is 50% to 90% in size by volume of the second reactor.

Lastly, embodiments may include a method of manufacturing polyolefin, including: polymerizing olefin at a first temperature in a first reactor into a first polyolefin; discharging from the first reactor a first slurry comprising the first polyolefin; cooling a feed stream; combining the feed stream with at least a portion of the first slurry to form a transfer slurry; feeding the transfer slurry to a second reactor; and polymerizing olefin at a second temperature in the second reactor into a second polyolefin, wherein the first temperature is greater than the second temperature. The first slurry and the transfer slurry may have a temperature difference of at least 3° F., 5° F., 10° F., 15° F., 20° F., or more. The method may include discharging from the second reactor a second slurry having the first polyolefin and the second polyolefin.

Additional Disclosure

Methods and systems for the production for polyolefin have been described. The following clauses are offered as further description:

Embodiment A

A polyolefin production system comprising: a first reactor configured to produce a first reactor discharge comprising a first polyolefin: a second reactor configured to produce a second reactor discharge comprising a second polyolefin; and a reactor transfer zone configured to receive the first reactor discharge and transfer at least a portion of the first reactor discharge to the second reactor as a second reactor transfer feed, wherein the first reactor discharge and the second reactor transfer feed have a temperature difference of at least 3° F.

Embodiment B

The polyolefin production system of embodiment A, wherein the reactor transfer zone comprises a heat exchanger.

Embodiment C

The polyolefin production system of embodiments A through B, wherein the reactor transfer zone comprises a slurry transfer line for the second reactor transfer feed, the slurry transfer line having a jacket for a cooling medium.

Embodiment D

The polyolefin production system of embodiments A through C, wherein the reactor transfer zone is configured to receive a cooling medium to remove heat from the second reactor transfer feed, and wherein the temperature difference is at least 10° F.

Embodiment E

The polyolefin production system of embodiments A through D, wherein the reactor transfer zone comprises a vessel configured for evaporative cooling to lower a temperature of the second reactor transfer feed.

Embodiment F

The polyolefin production system of embodiments A through E, wherein the first polyolefin has a different average molecular weight than the second polyolefin, and wherein the first polyolefin has a different density than the second polyolefin.

Embodiment G

The polyolefin production system of embodiments A through F, wherein the first polyolefin is a low molecular weight-high density polyolefin, and the second polyolefin is a high molecular weight-low density polyolefin.

Embodiment H

A polyolefin production system comprising: a first reactor configured to produce a transfer slurry comprising a first polyolefin polymerized in the first reactor; a heat exchanger configured to remove heat from the transfer slurry; and a second reactor configured to receive the transfer slurry cooled by the heat exchanger, and to produce a product slurry comprising a product polyolefin having the first polyolefin and a second polyolefin polymerized in the second reactor.

Embodiment I

The polyolefin production system of embodiment H, wherein the heat exchanger is configured to receive a cooling medium, and wherein the heat exchanger comprises a jacketed pipe heat exchanger, a shell-and-tube heat exchanger, a plate-and-frame heat exchanger, or any combination thereof.

Embodiment J

The polyolefin production system of embodiments H through I, comprising a transfer line to route the transfer slurry to the second reactor, wherein the heat exchanger is disposed along the transfer line.

Embodiment K

The polyolefin production system of embodiments H through J, wherein the first polyolefin has a different molecular weight than the second polyolefin, and wherein the first polyolefin has a different density than the second polyolefin.

Embodiment L

The polyolefin production system of embodiments H through K, comprising an additional heat exchanger configured to remove heat from a feed stream other than the transfer slurry to the second reactor.

Embodiment M

The polyolefin production system of embodiments H through L, wherein the feed stream is a diluent feed stream.

Embodiment N

The polyolefin production system of embodiments H through M, wherein the feed stream comprises monomer or comonomer, or both.

Embodiment O

A method of operating a polyolefin manufacturing system, comprising: producing a first polyolefin in a first polymerization reactor; cooling a transfer slurry comprising the first polyolefin from the first polymerization reactor; introducing the transfer slurry into a second polymerization reactor, producing a second polyolefin in the second polymerization reactor; and discharging from the second polymerization reactor a slurry comprising the first polyolefin and the second polyolefin.

Embodiment P

The method of embodiment O, wherein cooling the transfer slurry comprises receiving a cooling medium to cool the transfer slurry.

Embodiment Q

The method of embodiments O through P, comprising receiving a cooling medium at a heat exchanger, and wherein cooling the transfer slurry comprises subjecting the transfer slurry to the heat exchanger.

Embodiment R

The method of embodiments O through Q, comprising routing the transfer slurry through a first portion of a transfer line to a heat exchanger, and wherein cooling the transfer slurry comprises removing heat from the transfer slurry via the heat exchanger.

Embodiment S

The method of embodiments O through R, wherein cooling the transfer slurry comprises evaporation cooling of the transfer slurry.

Embodiment T

The method of embodiments O through S, wherein the evaporation cooling comprises flashing diluent in the transfer slurry.

Embodiment U

The method of embodiments O through T, wherein producing the first polyolefin comprises polymerizing olefin at a first temperature in the first polymerization reactor, and producing the second polyolefin comprises polymerizing olefin at a second temperature in the second polymerization reactor, wherein the first temperature is greater than the second temperature.

Embodiment V

The method of embodiments O through U, wherein the slurry discharged from the second polymerization reactor comprises a product polyolefin having the first polyolefin and the second polyolefin.

Embodiment W

The method of embodiments O through V, wherein the product polyolefin comprises a bimodal polyolefin.

Embodiment X

The method of embodiments O through W, wherein the first polyolefin comprises a high density polyethylene, and the second polyolefin comprises a low density polyethylene.

Embodiment Y

The method of embodiments O through X, comprising cooling a feed stream to the second polymerization reactor.

Embodiment Z

The method of embodiments O through Y, wherein the first polymerization reactor and the second polymerization reactor are substantially the same size in volume.

Embodiment AA

The method of embodiments O through Z, wherein the first polymerization reactor and the second polymerization reactor differ in size by volume.

Embodiment AB

The method of embodiments O through AA, wherein the first polymerization reactor is 50% to 90% in size by volume of the second polymerization reactor.

What is claimed is:

1. A polyolefin production system comprising:
a first loop slurry reactor;
a control system configured to control the first loop slurry reactor to produce a first reactor discharge slurry comprising solid particles of a first polyolefin, the first reactor discharge slurry having a discharge temperature;
a second loop slurry reactor, wherein the control system is configured to control the second loop slurry reactor at a second temperature to produce a second reactor discharge comprising solid particles of a second polyolefin; and
a reactor transfer zone configured to receive the first reactor discharge slurry and transfer at least a portion of the first reactor discharge slurry to the second loop slurry reactor as a second reactor transfer feed slurry, wherein the control system is configured to control the reactor transfer zone to cool the second reactor transfer feed slurry to the second temperature less than the discharge temperature, wherein the reactor transfer zone comprises at least one heat exchanger comprising a cooling medium to cool the first reactor discharge slurry or the second reactor transfer feed slurry, and wherein the control system is configured to control the first loop slurry reactor and the reactor transfer zone to cause the discharge temperature of the first reactor discharge slurry and the second temperature of the second reactor transfer feed slurry to have a temperature difference of at least 3° F., wherein no portion of the first reactor discharge slurry is recycled into either the first reactor discharge slurry or the first loop slurry reactor, and wherein the second reactor discharge or a portion thereof is not recycled into the first reactor discharge slurry, the second reactor transfer feed slurry, or the first or second loop slurry reactors.

2. The polyolefin production system of claim 1, wherein the reactor transfer zone comprises a slurry transfer line for the second reactor transfer feed slurry, and wherein the at least one heat exchanger comprises at least one jacket configured to receive the cooling medium.

3. The polyolefin production system of claim 1, wherein the at least one heat exchanger is configured to receive a cooling medium to remove heat from the second reactor transfer feed slurry, and wherein the temperature difference is at least 10° F.

4. The polyolefin production system of claim 1, wherein the at least one heat exchanger comprises a vessel configured for evaporative cooling to lower the temperature of the second reactor transfer feed slurry.

5. The polyolefin production system of claim 1, wherein the first polyolefin has a different average molecular weight than the second polyolefin, and wherein the first polyolefin has a different density than the second polyolefin.

6. The polyolefin production system of claim 1, wherein the first polyolefin is a low molecular weight-high density polyolefin, and the second polyolefin is a high molecular weight-low density polyolefin.

7. The polyolefin production system of claim 1, wherein the first polyolefin is polymerized in the first loop slurry reactor at a first temperature and the second polyolefin is polymerized in the second loop slurry reactor at the second temperature, in which the first temperature is greater than the second temperature.

8. A polyolefin production system comprising:
a first loop slurry reactor;
a control system configured to control the first loop slurry reactor to produce a transfer slurry comprising solid particles of a first polyolefin polymerized in the first loop slurry reactor, the transfer slurry having a discharge temperature;

a heat exchanger configured to transfer heat from the transfer slurry to a cooling medium, wherein the control system is configured to control the heat exchanger to cool the transfer slurry to a second temperature less than the discharge temperature; and a second loop slurry reactor configured to receive the transfer slurry cooled by the heat exchanger to the second temperature below the discharge temperature, wherein the control system is configured to control the second loop slurry reactor at the second temperature to produce a product slurry comprising solid particles of a product polyolefin having the first polyolefin and a second polyolefin polymerized in the second loop slurry reactor, wherein no portion of the transfer slurry is recycled into either the transfer slurry or the first loop slurry reactor, and wherein the product slurry or a portion thereof is not recycled into the transfer slurry or the first or second loop slurry reactors.

9. The polyolefin production system of claim 8, wherein the heat exchanger is configured to receive a cooling medium, and wherein the heat exchanger comprises a jacketed pipe heat exchanger, a shell-and-tube heat exchanger, a plate-and-frame heat exchanger, or any combination thereof.

10. The polyolefin production system of claim 8, comprising a transfer line to route the transfer slurry to the second loop slurry reactor, wherein the heat exchanger is disposed along the transfer line.

11. The polyolefin production system of claim 8, wherein the first polyolefin has a different molecular weight than the second polyolefin, and wherein the first polyolefin has a different density than the second polyolefin.

12. The polyolefin production system of claim 8, comprising an additional heat exchanger configured to remove heat from a feed stream other than the transfer slurry to the second loop slurry reactor.

13. The polyolefin production system of claim 12, wherein the feed stream is diluent feed stream.

14. The polyolefin production system of claim 12, wherein the feed stream comprises monomer or comonomer, or both.

15. The polyolefin production system of claim 8, wherein the second polyolefin is polymerized in the second loop slurry reactor at the second temperature that is less than the discharge temperature.

\* \* \* \* \*